(12) United States Patent
Liu et al.

(10) Patent No.: US 11,697,658 B2
(45) Date of Patent: Jul. 11, 2023

(54) METHOD FOR PREPARING LORNOXICAM

(71) Applicant: Beijing Jincheng Taier Pharmaceutical Co., Ltd., Beijing (CN)

(72) Inventors: Zhen Liu, Beijing (CN); Dongye Xing, Beijing (CN); Zhongzheng Zhang, Beijing (CN); Jie Li, Beijing (CN); Yangong Han, Beijing (CN); Yali Cui, Beijing (CN); Liru Wang, Beijing (CN); Hongliang Liu, Beijing (CN); Yan Mi, Beijing (CN); Li Li, Beijing (CN); Jingang Tang, Beijing (CN); Yi Kang, Beijing (CN)

(73) Assignee: Beijing Jincheng Taier Pharmaceutical Co., Ltd., Beijing (CN)

( * ) Notice: Subject to any disclaimer, the term of this patent is extended or adjusted under 35 U.S.C. 154(b) by 112 days.

(21) Appl. No.: 17/383,493

(22) Filed: Jul. 23, 2021

(65) Prior Publication Data

US 2022/0204529 A1 Jun. 30, 2022

(30) Foreign Application Priority Data

Dec. 25, 2020 (CN) .......................... 202011558454.2

(51) Int. Cl.
*C07D 513/04* (2006.01)

(52) U.S. Cl.
CPC .................................. *C07D 513/04* (2013.01)

(58) Field of Classification Search
CPC ..................................................... C07D 513/04
USPC ........................................................ 514/226.5
See application file for complete search history.

(56) References Cited

FOREIGN PATENT DOCUMENTS

CN 106892932 A 6/2017

*Primary Examiner* — Kahsay Habte
(74) *Attorney, Agent, or Firm* — Myers Bigel, P.A.

(57) ABSTRACT

The present disclosure relates to the technical field of drug synthesis, in particular to a method for preparing lornoxicam. The method includes the following steps: using 6-chloro-4-hydroxy-2-methyl-2-H-thieno[2,3-e]-1,2-thiazine methyl carboxylate-1,1-dioxide and 2-aminopyridine as raw materials, and xylene as a solvent; mixing the raw material and solvent, and adding a stabilizer, to obtain a mixture; subjecting the mixture to an ammonolysis; cooling the resulting reactant; conducting a vacuum concentration to remove the solvent; adding an organic solvent and slurrying, and filtering, to obtain a crude lornoxicam; and refining the crude lornoxicam to obtain the lornoxicam. In the present disclosure, p-toluenesulfonic acid is used as a stabilizer to reduce the reaction temperature and promote the reaction to proceed forward, thereby improving the quality and yield of the product.

10 Claims, 5 Drawing Sheets

METHOD FOR PREPARING LORNOXICAM

CROSS REFERENCE TO RELATED APPLICATION(S)

This patent application claims the benefit and priority of Chinese Patent Application No. 202011558454.2 filed on Dec. 25, 2020, the disclosure of which is incorporated by reference herein in its entirety as part of the present application.

TECHNICAL FIELD

The present disclosure relates to the technical field of drug synthesis, in particular to a method for preparing lornoxicam.

BACKGROUND ART

With the rapid development of artificial intelligence technology and industrial modernization, the quality of life and health have been constantly improved. For many diseases and various pains that plague humans, especially pain caused by cancer, postoperative pain, osteoarthritis pain, a large number of anti-inflammatory and analgesic drugs are needed. Currently, in order to treat moderate or severe pain, drugs like tramadol, morphine and dulantin are used, but they have side effects such as addiction, respiratory depression and sedation, and thus their application are controlled by hospitals.

Lornoxicam developed by Nycomed Company, Norway, was first listed in Denmark in October 1997, with forms of tablets, intravenous injections and intramuscular injections. Lornoxicam exhibits a desirable clinical effect on moderate and severe lumbago, rheumatoid arthritis, postoperative pain, and osteoarthritis pain. Due to its excellent analgesic effect, the lornoxicam was commercially available in 2002 in Chinese market, exhibiting obvious and strong analgesic effect. Lornoxicam, as a clinically safe analgesic, has an analgesic effect of opioids without causing adverse reactions or addictive side effects, and makes it possible to activate the central opioid peptide system and trigger the release of endorphins and the like, thereby showing a significant analgesic effect. Due to the desirable social and economic benefits achieved by Lornoxicam, a research on the synthesis of Lornoxicam is needed.

At present, there are many methods for preparing lornoxicam, mainly including the following two routes:

Route 1: 2,5-dichlorothiophene was used as a starting material by Nycomed Company, Norway, in 1997 to synthesize lornoxicam through a 7-step reaction:

The above synthesis route has many steps, relatively low total yield and serious pollution. In the synthesis route, reagents such as n-butyllithium, chlorosulfonic acid and phosphorus pentachloride were used, and they were not suitable for industrial production; in the last step, 6-chloro-4-hydroxy-2-methyl-2-H-thieno[2,3-e]-1,2-thiazine methyl carboxylate-1,1-dioxide was used as a raw material, and 2-aminopyridine was added thereto, and the resulting mixture was subjected to an ammonolysis, where xylene as a solvent is used in a huge amount, with a volume of 50-100 V. The above synthesis route has a lot of side reaction, long reaction time, and non-ideal yield, with a total yield of about 0.45%.

Route 2: In a Chinese patent CN106892932A made by Vocational and Technical College of Engineering, Jiangsu, China, in 2017, a process for preparing lornoxicam is provided as follows:

In this route, in the first step, Boc-sarcosine and 2-aminopyridine were subjected to a condensation to obtain an intermediate 2-N-methyl-2-N-Boc-acetyl(2-pyridyl)amine (I), and then the resulting reactant was subjected to a treatment to remove protective groups by utilizing a solution of hydrogen chloride in ethyl acetate. In the second step, the resulting reactant obtained by the first step was dissolved in ethyl acetate, an acid binding agent was added thereto, and a solution of 5-chloro-3-chlorosulfonylthiophene-2-methyl carbonate in ethyl acetate was added dropwise at ambient temperature, and the resulting mixture was subjected to a reaction to obtain 5-chloro-3-[[N-methyl-N-(acetamidopyridine)]sulfonyl]-2-thiophene methyl formate (II). In the third step, 5-chloro-3-[[N-methyl-N-(acetamidopyridine)]sulfonyl]-2-thiophene methyl formate (II) was dissolved in alcohol, and a corresponding sodium alkoxide was added thereto, and the resulting reactant was subjected to an intramolecular Claisen condensation under reflux to obtain the lornoxicam.

Route 2 is relatively novel, simplifies the process route and shortens the synthesis steps. However, in the last step of synthesizing lornoxicam, due to the steric hindrance in 5-chloro-3-[[N-methyl-N-(acetamidopyridine)]sulfonyl]-2-thiophene methyl formate, the intermolecular ring closure reaction has a low yield, and the demand for the corresponding metal alkali is too high. The reaction has a long time and a relatively high energy demand.

The amido bond as a common bond in various drug molecules is commonly obtained by a dehydration condensation of carboxyl groups and amino groups, as well as an ammonolysis of ester of amino-containing raw materials and ester groups. In the prior art, the preparation of lornoxicam is carried out at a relatively high temperature, generally more than 140° C., and thus it is required to increase amount of solvent to reduce severe coking in the reaction liquid. Moreover, the reaction carried out at high temperature would destroy the stability of the reaction material 2-aminopyridine, resulting in an increase in reaction by-products and a decrease in yield.

SUMMARY

The purpose of the present disclosure is to provide a method for preparing lornoxicam, in which p-toluenesulfonic acid is used as a stabilizer to reduce the reaction temperature and promote the reaction to proceed forward, thereby improving the quality and yield of the product. Meanwhile, the method according to the present disclosure has a lower amount of industrial solvent, an optimized post-treatment process and a reduced treatment cost of waste water, waste gas, and solid waste.

In order to solve the above technical problem, the present disclosure provides the following technical solution:

The method for preparing lornoxicam includes the following steps: using 6-chloro-4-hydroxy-2-methyl-2-H-thieno[2,3-e]-1,2-thiazine methyl carboxylate-1,1-dioxide and 2-aminopyridine as raw materials, and xylene as a solvent; mixing the raw materials and the solvent, and adding a stabilizer, to obtain a mixture; subjecting the mixture to an ammonolysis by heating and reflux; cooling the resulting reactant; conducting a vacuum concentration to remove the solvent; adding an organic solvent and slurrying, and filtering, to obtain a crude lornoxicam; and refining the crude lornoxicam to obtain the lornoxicam.

In some embodiments, a molar ratio of the stabilizer to 6-chloro-4-hydroxy-2-methyl-2-H-thieno[2,3-e]-1,2-thiazine methyl carboxylate-1,1-dioxide is in the range of (0.05-1.5):1, and the stabilizer is p-toluenesulfonic acid.

In some embodiments, a molar ratio of 6-chloro-4-hydroxy-2-methyl-2-H-thieno[2,3-e]-1,2-thiazine methyl carboxylate-1,1-dioxide to 2-aminopyridine is in the range of 1:(1-2); a ratio of the mass of 6-chloro-4-hydroxy-2-methyl-2-H-thieno[2,3-e]-1,2-thiazine methyl carboxylate-1,1-dioxide to the volume of xylene is in the range of 1 g:(20-30) mL.

In some embodiments, the ammonolysis is conducted at a temperature of 100-130° C. for 4-6 hours; the vacuum concentration is conducted at a temperature of 50-80° C., and a pressure of −0.07 MPa to −0.1 MPa.

In some embodiments, a ratio of the volume of the organic solvent to the mass of 6-chloro-4-hydroxy-2-methyl-2-H-thieno[2,3-e]-1,2-thiazine methyl carboxylate-1,1-dioxide is in the range of (5-6) mL:1 g, preferably 5 mL:1 g; the organic solvent is a mixed solvent of dichloromethane and methanol with a volume ratio of 4:1.

In some embodiments, the slurrying is conducted at a temperature of 50-80° C. for 1-5 hours.

The method according to the present disclosure further comprises: subjecting the reaction system to cooling and a vacuum concentration to remove the solvent to obtain a concentrate in which the ratio of the mass of 6-chloro-4-hydroxy-2-methyl-2-H-thieno[2,3-e]-1,2-thiazine methyl carboxylate-1,1-dioxide to the volume of the concentrate is in the range of 1 g:(3-5) mL; adding an organic solvent after cooling to 20° C. to 30° C., heating to a slurrying temperature, slurrying, and cooling to 20° C. to 30° C. and filtering to obtain the crude lornoxicam; after subjecting the reaction system to the vacuum concentration, namely after adding 1 g of 6-chloro-4-hydroxy-2-methyl-2-H-thieno[2,3-e]-1,2-thiazine methyl carboxylate-1,1-dioxide, subjecting the reaction liquid in the reaction system to a vacuum concentration to 3-5 mL.

In the present disclosure, the refining specifically comprises: adding the crude lornoxicam into an organic mixed solvent, heating to make the crude lornoxicam dissolve in the organic mixed solvent until the resulting solution is clear, decoloring, maintaining temperature for growing crystals, cooling for crystallization, conducting a vacuum filtration, and drying, to obtain the lornoxicam.

In some embodiments, a ratio of the volume of the organic mixed solvent to the mass of the crude lornoxicam is in the range of (35-75) mL:1 g; the organic mixed solvent is a mixed solvent of xylene, methanol or dichloromethane and 1,4-dioxane. In some embodiments, the organic mixed solvent is a mixed solvent of xylene and 1,4-dioxane. In some embodiments, a volume ratio of xylene, methanol or dichloromethane to 1,4-dioxane is 1:14.

In some embodiments, the decoloring is conducted with an activated carbon under reflux for 1-5 hours; a mass ratio of the activated carbon to the crude lornoxicam is in the range of (0.05-0.06):1; and the process of maintaining temperature for growing crystals is conducted at a temperature of 100° C. to 110° C. for 1-5 hours.

In some embodiments, the cooling for crystallization is conducted at a temperature of 15-50° C.; the vacuum filtration is conducted at a temperature of 15-30° C.; the drying is conducted at a temperature of 50-60° C. for 22-24 hours.

The method of the present disclosure is carried out according to the following route:

In the present disclosure, 6-chloro-4-hydroxy-2-methyl-2-H-thieno[2,3-e]-1,2-thiazine methyl carboxylate-1,1-dioxide and 2-aminopyridine are used as raw materials, xylene is used as a solvent, and p-toluenesulfonic acid is used as a stabilizer, they are mixed to obtain a mixture, and the mixture is subjected to an ammonolysis by heating and reflux, where the ammonolysis is a nucleophilic substitution reaction, having a reaction mechanism as follows:

In the presence of p-toluenesulfonic acid, a carbonyl oxygen atom on 6-chloro-4-hydroxy-2-methyl-2-H-thieno [2,3-e]-1,2-thiazine methyl carboxylate-1,1-dioxide molecule is protonated by a hydrogen ion to form an oxonium ion INT-1. A nitrogen atom in 2-aminopyridine contains a lone pair of electrons, and a carbonyl carbon atom is attacked by the nitrogen atom in 2-aminopyridine to form an intermediate INT-2. The intermediate INT-2 has a unstable hydrogen proton on nitrogen atoms, and is subjected to a proton transfer to form an intermediate INT-3, and then the intermediate INT-3 is stripped of a molecule of methanol to form an intermediate INT-4. Finally, an enol interconversion structure of the intermediate INT-4 forms a lornoxicam molecule. In the present disclosure, p-toluenesulfonic acid is used as the stabilizer, having a desirable catalytic effect, reducing the activation energy required for the reaction, and promoting the reaction to proceed forward, as well as reducing the temperature required for the reaction, shortening the reaction time, and improving production effectiveness.

The the present disclosure has the following beneficial effects:

(1) In the presence of p-toluenesulfonic acid, the carbonyl oxygen atom on 6-chloro-4-hydroxy-2-methyl-2-H-thieno [2,3-e]-1,2-thiazine methyl carboxylate-1,1-dioxide molecule is protonated by hydrogen ion to form an oxonium ion, which improves the activity of the carbonyl carbon atom. Meanwhile, p-toluenesulfonic acid could increase the nucleophilicity of 2-aminopyridine and promote the reaction between the nitrogen atom in 2-aminopyridine and the carbonyl carbon atom. Under the condition that relatively strong protic acids such as acetic acid and hydrochloric acid are used, hydrogen ions and 2-aminopyridine would form an ammonium salt due to the relatively strong acidity of the reaction environment, so as to reduce the nucleophilicity of 2-aminopyridine, resulting in a relatively low conversion rate of raw materials to affect the yield of the reaction. In the present disclosure, p-toluenesulfonic acid is used as the stabilizer, having a desirable catalytic effect, reducing the activation energy required for the reaction, and reducing the temperature required for the reaction, as well as promoting the reaction to proceed forward, shortening the reaction time, and improving production effectiveness and product yield.

(2) The present disclosure makes it possible to reduce the temperature of the ammonolysis, reduce the amount of xylene organic solvent, avoid the occurrence of coking during the reaction process, save the production cost of the factory, and save energy.

(3) In the present disclosure, there is no dangerous gas generation during the reaction process, and no need to distill out solvents such as methanol and xylene at high temperature for a long time, greatly shortening the reaction time, and reducing the generation of side reactions, so as to improve the production environment, ensure the production safety, and is suitable for industrial production.

(4) The present disclosure adopts a mixed solution of dichloromethane and methanol for slurrying, and adopts a mixed solvent of xylene, methanol or dichloromethane and 1,4-dioxane for recrystallization, thus having less solvent consumption, high purification yield, and environment protection.

DETAILED DESCRIPTION OF THE EMBODIMENTS

The present disclosure will be further described below with reference to examples.

Example 1

Under nitrogen, 200 mL of xylene, 10 g of 6-chloro-4-hydroxy-2-methyl-2-H-thieno[2,3-e]-1,2-thiazine methyl carboxylate-1,1-dioxide, 3.65 g of 2-aminopyridine, and 0.6 g of p-toluenesulfonic acid were added into a 500 mL four-neck flask. The above materials were heated to 130° C., and then subjected to an ammonolysis at this temperature for 4 hours. The resulting reactant was sampled to conduct a HPLC (High Performance Liquid Chromatography) detection. When the content of 6-chloro-4-hydroxy-2-methyl-2-H-thieno[2,3-e]-1,2-thiazine methyl carboxylate-1,1-dioxide was less than or equal to 2%, the reaction was terminated.

Figure 1:
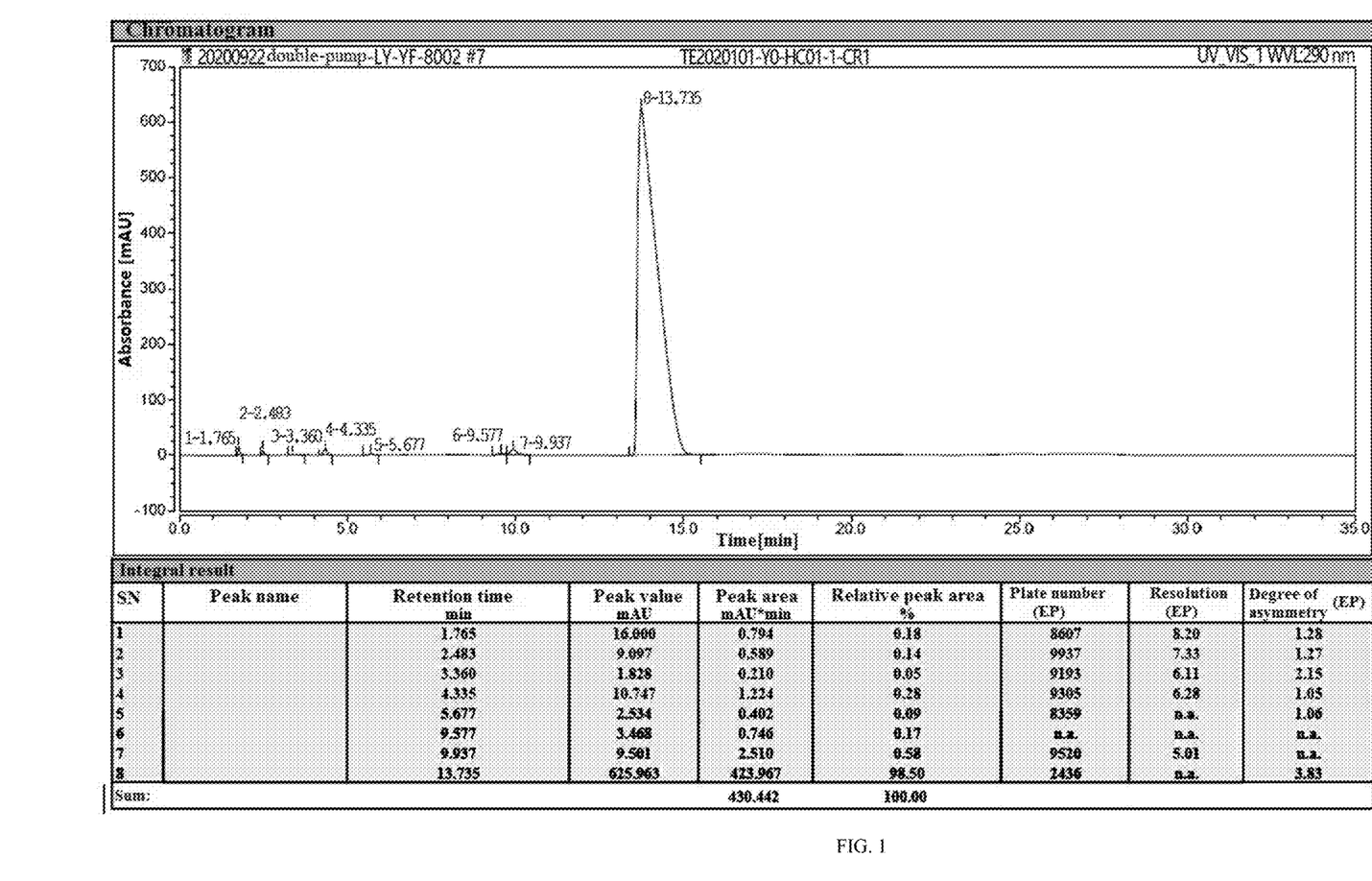
FIG. 1 shows a chromatogram diagram of the crude lornoxicam as prepared in Example 1.

The reaction solution was cooled to 50° C., and then subjected to a vacuum concentration at this temperature and a pressure of −0.07 MPa to remove the solvent, and the vacuum concentration was stopped after the reaction solution was concentrated to 30 mL. The resulting reaction solution was cooled to 20° C., and 50 mL of a mixed solution of dichloromethane and methanol was added, where a volume ratio of dichloromethane to methanol was 4:1. The mixed reaction solution was then heated up to 80° C., and subjected to a slurrying at this temperature for 2 hours, and then was cooled to 30° C. and filtered, obtaining a crude lornoxicam. The crude lornoxicam had a wet weight of 10.8 g, a purity of 98.50%, a yield of 88.65%, and a chromatogram shown in FIG. 1.

Figure 2:
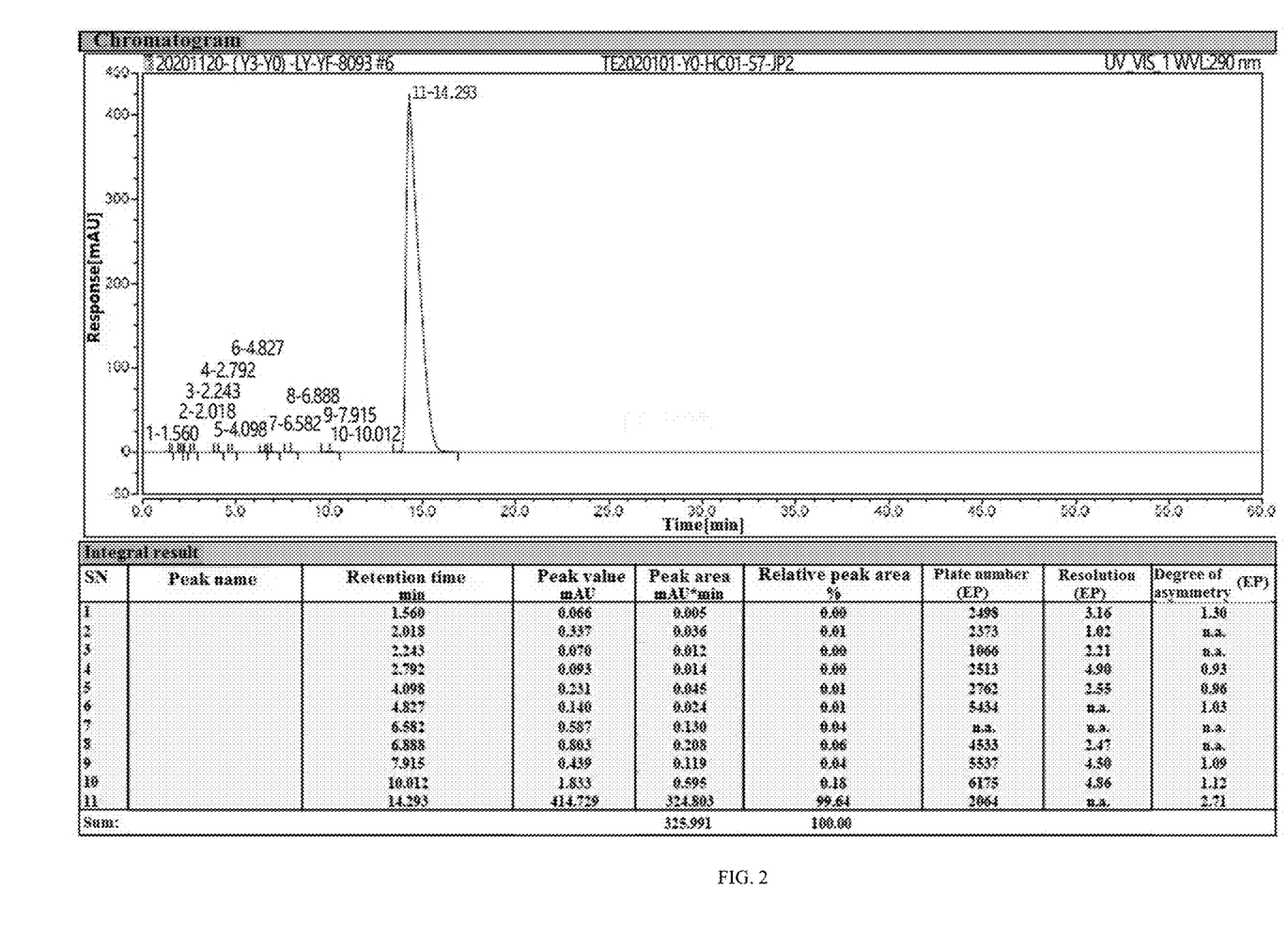
FIG. 2 shows a chromatogram diagram of the refined lornoxicam as prepared in Example 1.

Under nitrogen, 10.8 g of the crude lornoxicam was added into a 500 mL four-neck flask, and 378 mL of a mixed solvent of xylene and 1,4-dioxane was added, where a volume ratio of xylene to 1,4-dioxane was 1:14. The resulting mixture was heated to make the crude lornoxicam dissolve in the mixed solvent until the resulting solution was clear. At this state, 0.6 g of activated carbon was added thereto. Then the resulting mixture was decolored under reflux for 2 hours, and subjected to a process of maintaining temperature for growing crystals at 100° C. for 5 hours, and then filtered under heat preservation to collect a filtrate. The filtrate was cooled to 50° C. while stirring to precipitate a yellow solid of lornoxicam, then was filtered under vacuum at 15° C., to obtain a filter cake with a wet weight of 11.2 g. The filter cake was subjected to a vacuum drying in a vacuum oven at 60° C. under a pressure of −0.07 MPa for 24 hours, to obtain 10.5 g of yellow solid lornoxicam. The yellow solid lornoxicam was sampled to conduct a HPLC detection, and the result showed that the sample had a purity of 99.64%, a yield of 96.87%, and a chromatogram shown in FIG. 2.

Example 2

Under nitrogen, 400 mL of xylene, 20 g of 6-chloro-4-hydroxy-2-methyl-2-H-thieno[2,3-e]-1,2-thiazine methyl carboxylate-1,1-dioxide, 7.3 g of 2-aminopyridine, and 1.2 g of p-toluenesulfonic acid were added into a 1 L four-neck flask. The above materials were heated to 115° C., and then subjected to an ammonolysis at this temperature for 5 hours. The resulting reactant was sampled to conduct a HPLC (High Performance Liquid Chromatography) detection. When the content of 6-chloro-4-hydroxy-2-methyl-2-H-thieno[2,3-e]-1,2-thiazine methyl carboxylate-1,1-dioxide was less than or equal to 2%, the reaction was terminated.

The reaction solution was cooled to 65° C., and then subjected to a vacuum concentration at this temperature and a pressure of −0.09 MPa to remove the solvent, and the vacuum concentration was stopped after the reaction solution was concentrated to 100 mL. The resulting reaction solution was cooled to 25° C., and 100 mL of a mixed solution of dichloromethane and methanol was added, where a volume ratio of dichloromethane to methanol was 4:1. The mixed reaction solution was then heated up to 65° C., and subjected to a slurrying at this temperature for 3 hours, and then was cooled to 25° C. and filtered, obtaining a crude lornoxicam. The crude lornoxicam had a wet weight of 20.6 g, a purity of 98.6%, and a yield of 84.63%.

Figure 3:
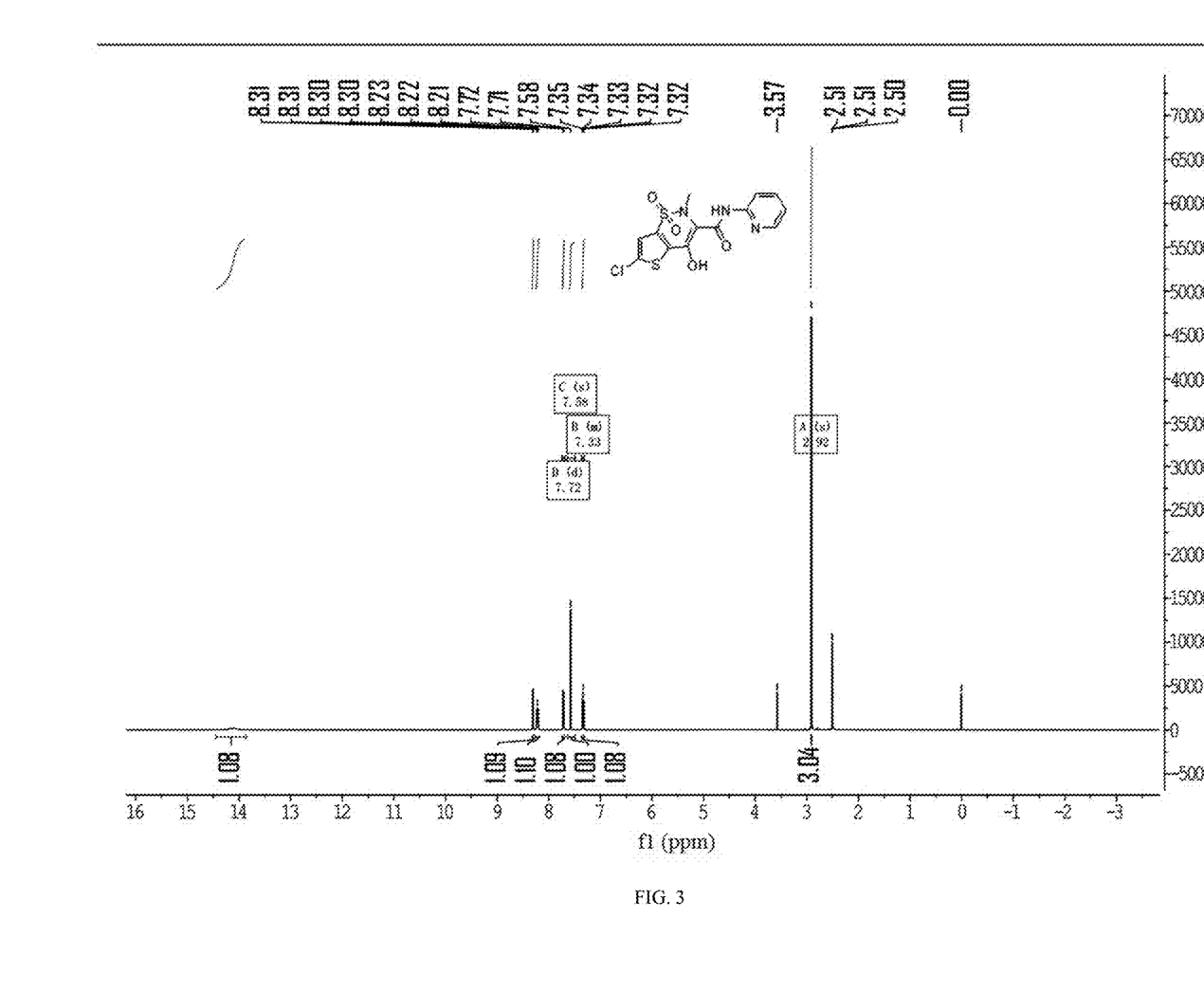
FIG. 3 shows an HNMR spectrum of the refined lornoxicam as prepared in Example 2.

Under nitrogen, 20.6 g of the crude lornoxicam was added into a 1 L four-neck flask, and 745.5 mL of a mixed solvent of xylene and 1,4-dioxane was added, where a volume ratio of xylene to 1,4-dioxane was 1:14. The resulting mixture was heated to make the crude lornoxicam dissolve in the mixed solvent until the resulting solution was clear. At this state, 1.2 g of activated carbon was added thereto. Then the resulting mixture was decolored under reflux for 1 hour, and subjected to a process of maintaining temperature for growing crystals at 105° C. for 3 hours, and then filtered under heat preservation to collect a filtrate. The filtrate was cooled to 30° C. while stirring to precipitate a yellow solid of lornoxicam, then was filtered under vacuum at 20° C., to obtain a filter cake with a wet weight of 22.8 g. The filter cake was subjected to a vacuum drying in a vacuum oven at 55° C. under a pressure of −0.09 MPa for 23 hours, to obtain 20.3 g of yellow solid lornoxicam. The yellow solid lornoxicam was sampled to conduct a HPLC detection, and the result showed that the sample had a purity of 99.4%, a yield of 97.95%, and an HNMR (Hydrogen Nuclear Magnetic Resonance) spectrum shown in FIG. 3.

Example 3

Under nitrogen, 800 mL of xylene, 40 g of 6-chloro-4-hydroxy-2-methyl-2-H-thieno[2,3-e]-1,2-thiazine methyl carboxylate-1,1-dioxide, 14.6 g of 2-aminopyridine, and 2.4 g of p-toluenesulfonic acid were added into a 2 L four-neck flask. The above materials were heated to 110° C., and then subjected to an ammonolysis at this temperature for 6 hours. The resulting reactant was sampled to conduct a HPLC (High Performance Liquid Chromatography) detection. When the content of 6-chloro-4-hydroxy-2-methyl-2-H-thieno[2,3-e]-1,2-thiazine methyl carboxylate-1,1-dioxide was less than or equal to 2%, the reaction was terminated.

The reaction solution was cooled to 80° C., and then subjected to a vacuum concentration at this temperature and a pressure of −0.1 MPa to remove the solvent, and the vacuum concentration was stopped after the reaction solution was concentrated to 120 mL. The resulting reaction solution was cooled to 30° C., and 200 mL of a mixed solution of dichloromethane and methanol was added, where a volume ratio of dichloromethane to methanol was 4:1. The mixed reaction solution was then heated up to 50° C. and subjected to a slurrying at this temperature for hours, and then was cooled to 20° C. and filtered, obtaining a crude lornoxicam. The crude lornoxicam had a wet weight of 40.9 g, a purity of 98.8%, and a yield of 84.18%.

Under nitrogen, 40.9 g of the crude lornoxicam was added into a 2 L four-neck flask, and 1571.5 mL of a mixed solvent of xylene and 1,4-dioxane was added, where a volume ratio of xylene to 1,4-dioxane was 1:14. The resulting mixture was heated to make the crude lornoxicam dissolve in the mixed solvent until the resulting solution was clear. At this state, 2.4 g of activated carbon was added thereto. Then the resulting mixture was decolored under reflux for 1 hour, and subjected to a process of maintaining temperature for growing crystals at 110° C. for 2 hours, and then filtered under heat preservation to collect a filtrate. The filtrate was cooled to 20° C. while stirring to precipitate a yellow solid of lornoxicam, then was filtered under vacuum at 30° C., to obtain a filter cake with a wet weight of 42.9 g. The filter cake was subjected to a vacuum drying in a vacuum oven at 50° C. under a pressure of −0.1 MPa for 24 hours, to obtain 39.1 g of yellow solid lornoxicam. The yellow solid lornoxicam was sampled to conduct a HPLC detection, and the result showed that the sample had a purity of 99.64%, a yield of 95.25%.

Comparative Example 1

Figure 4:
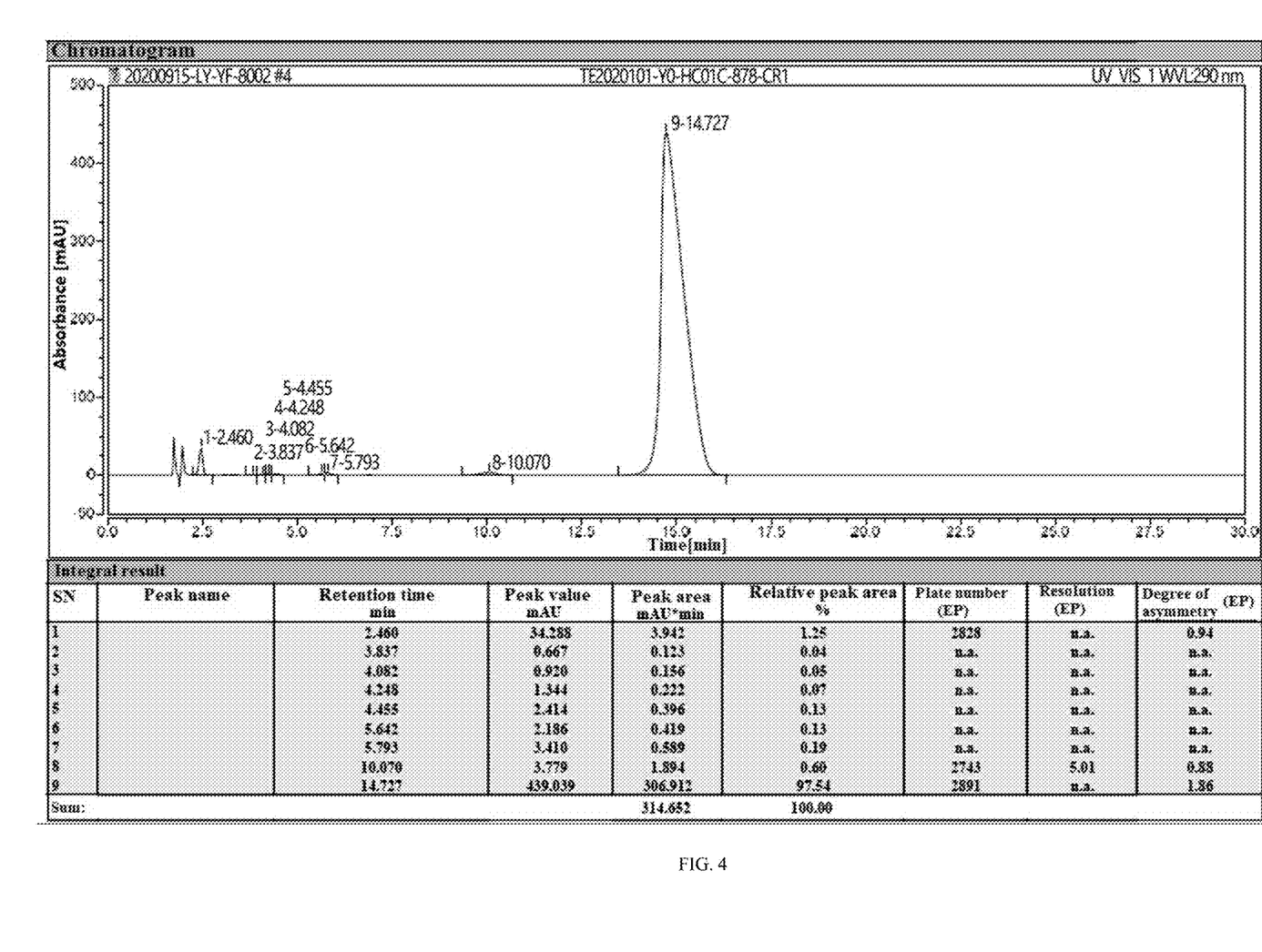
FIG. 4 shows a chromatogram diagram of the crude lornoxicam as prepared in Comparative Example 1.
Figure 5:
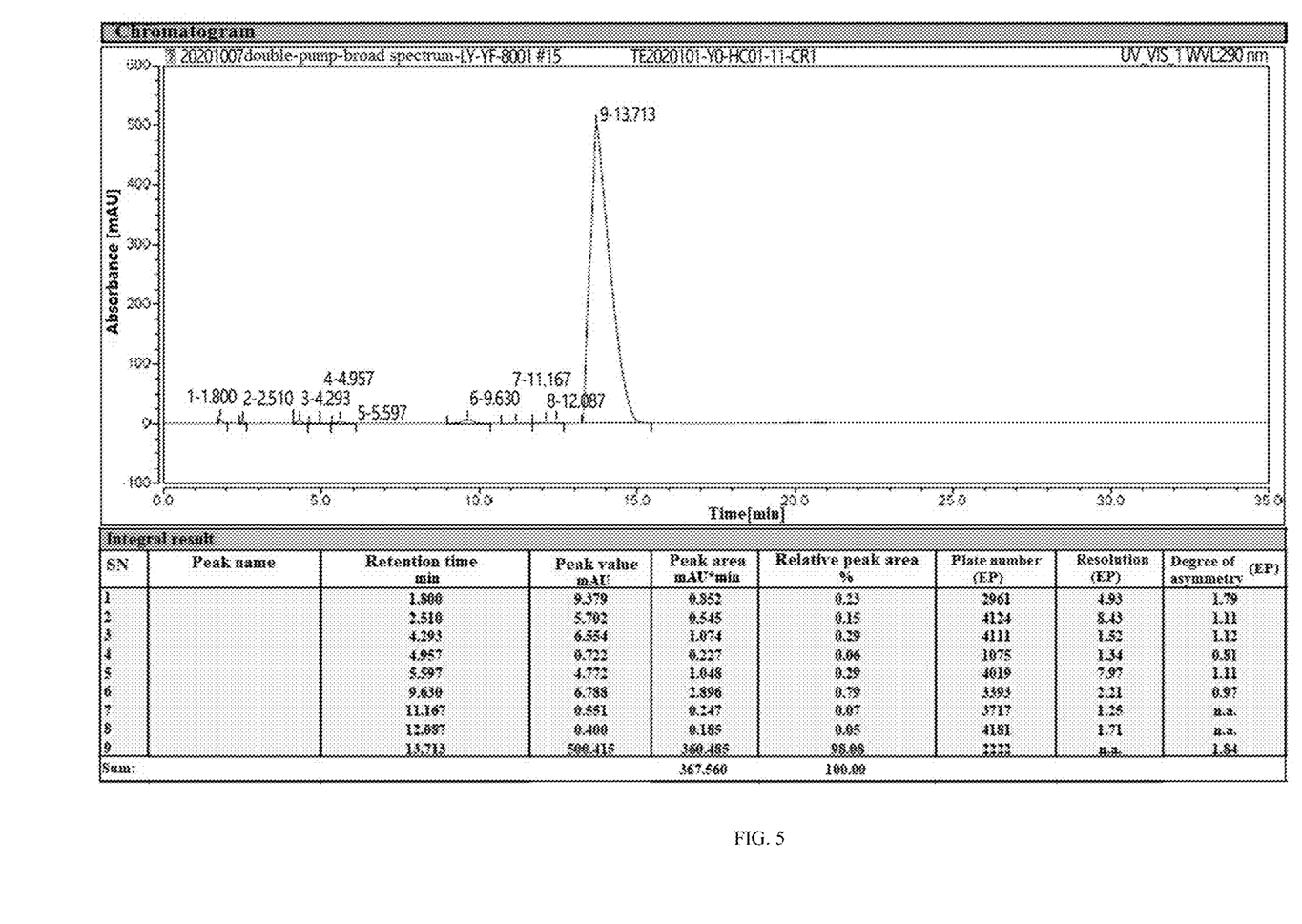
FIG. 5 shows a chromatogram diagram of the refined lornoxicam as prepared in Comparative Example 1.

Comparative Example 1 was carried out according to the procedures of Example 1, except that p-toluenesulfonic acid was not added. The crude lornoxicam as prepared in Comparative Example 1 had a wet weight of 5.9 g, a purity of 97.54%, a yield of 47.95%, and a chromatogram shown in FIG. 4. The refined lornoxicam obtained by refining the crude lornoxicam had a weight of 5.6 g, a purity of 98.08%, a yield of 93.09%, and a chromatogram shown in FIG. 5.

Comparative Example 2

Comparative Example 2 was carried out according to the procedures of Example 2, except that p-toluenesulfonic acid was not added. The crude lornoxicam as prepared in Comparative Example 2 had a wet weight of 11.28 g, a purity of 97.3%, and a yield of 45.73%. The refined lornoxicam obtained by refining the crude lornoxicam had a weight of 10.72 g, a purity of 98.2%, and a yield of 93.32%.

Comparative Example 3

Comparative Example 3 was carried out according to the procedures of Example 3, except that p-toluenesulfonic acid was not added. The crude lornoxicam as prepared in Comparative Example 3 had a wet weight of 24.12 g, a purity of 98.08%, and a yield of 49.28%. The refined lornoxicam obtained by refining the crude lornoxicam had a weight of 22.71 g, a purity of 98.88%, and a yield of 93.09%.

What is claimed is:
1. A method for preparing lornoxicam, comprising:
using 6-chloro-4-hydroxy-2-methyl-2-H-thieno[2,3-e]-1, 2-thiazine methyl carboxylate-1,1-dioxide and 2-aminopyridine as raw materials, and xylene as a solvent;
mixing the raw materials and the solvent, and adding a stabilizer, to obtain a mixture;
subjecting the mixture to an ammonolysis;
conducting a vacuum concentration to remove the solvent;
adding an organic solvent and slurrying, and filtering, to obtain a crude lornoxicam; and
refining the crude lornoxicam, to obtain the lornoxicam wherein the stabilizer is p-toluenesulfonic acid; and
the organic solvent is a mixed solvent of dichloromethane and methanol with a volume ratio of 4:1.

2. The method of claim 1, wherein a molar ratio of the stabilizer to 6-chloro-4-hydroxy-2-methyl-2-H-thieno[2,3-e]-1,2-thiazine methyl carboxylate-1,1-dioxide is in a range of (0.05-1.5):1.

3. The method of claim 1, wherein a molar ratio of 6-chloro-4-hydroxy-2-methyl-2-H-thieno[2,3-e]-1,2-thiazine methyl carboxylate-1,1-dioxide to 2-aminopyridine is in a range of 1:(1-2); and
wherein a ratio of the mass of 6-chloro-4-hydroxy-2-methyl-2-H-thieno[2,3-e]-1,2-thiazine methyl carboxylate-1,1-dioxide to the volume of xylene is in a range of 1 gram:(20-30) mL.

4. The method of claim 1, wherein the ammonolysis is conducted at a temperature of 100° C. to 130° C. for 4-6 hours; and
wherein the vacuum concentration is conducted at a temperature of 50° C. to 80° C. and a pressure of −0.07 MPa to −0.1 MPa.

5. The method of claim 1, wherein a ratio of the volume of the organic solvent to the mass of 6-chloro-4-hydroxy-2-methyl-2-H-thieno[2,3-e]-1,2-thiazine methyl carboxylate-1,1-dioxide is in a range of (5-6) mL:1 gram.

6. The method of claim 1, wherein the slurrying is conducted at a temperature of 50° C. to 80° C. for 1-3 hours.

7. The method of claim 1, wherein the refining comprises: adding the crude lornoxicam into an organic mixed solvent, heating to make the crude lornoxicam dissolve in the organic mixed solvent until a resulting solution is clear, decoloring, maintaining temperature for growing crystals, cooling for crystallization, conducting a vacuum filtration, and drying, to obtain the lornoxicam.

8. The method of claim 7, wherein a ratio of the volume of the organic mixed solvent to the mass of the crude lornoxicam is in a range of (35-75) mL:1 gram; the organic mixed solvent is a mixed solvent of xylene, methanol or dichloromethane and 1,4-dioxane, and wherein a volume ratio of xylene, methanol or dichloromethane to 1,4-dioxane is 1:14.

9. The method of claim 7, wherein the decoloring is conducted with an activated carbon; a mass ratio of the activated carbon to the crude lornoxicam is in a range of (0.05-0.06):1; and wherein the maintaining of the temperature for growing crystals is conducted at a temperature of 100° C. to 110° C. for 1-5 hours.

10. The method of claim 7, wherein the cooling for crystallization is conducted at a temperature of 15-50° C.; the vacuum filtration is conducted at a temperature of 15-30° C.; and wherein the drying is conducted at a temperature of 50-60° C. for 22-24 hours.

* * * * *